United States Patent [19]

Aurelian et al.

[11] Patent Number: 5,965,356
[45] Date of Patent: Oct. 12, 1999

[54] HERPES SIMPLEX VIRUS TYPE SPECIFIC SEROASSAY

[75] Inventors: Laure Aurelian, Baltimore; Cynthia Smith, Timonium, both of Md.

[73] Assignee: University of Maryland, Baltimore, Baltimore, Md.

[21] Appl. No.: 09/015,815

[22] Filed: Jan. 29, 1998

Related U.S. Application Data

[60] Provisional application No. 60/036,622, Jan. 31, 1997.
[51] Int. Cl.⁶ .......................... C12Q 1/70; G01N 33/53; A61K 39/12
[52] U.S. Cl. .................. 435/5; 435/7.1; 435/7.72; 435/7.9; 435/7.94; 424/204.1; 424/231.11
[58] Field of Search ................. 435/5, 7.1, 7.72, 435/7.9, 7.94; 424/204.1, 231.11

[56] References Cited

PUBLICATIONS

Aurelian et al, 1989, Cancer Cells, vol. 7, pp. 187–191.

*Primary Examiner*—Mary E. Mosher
*Assistant Examiner*—Ali R. Salimi
*Attorney, Agent, or Firm*—William S. Ramsey; Pepper Hamilton, LLP

[57] ABSTRACT

A recombinant virus (ICP10ΔRR) has been developed which is useful in a Western blot assay to specifically detect antibody to HSV-2, even the presence of co-existing antibody to HSV-1.

15 Claims, 2 Drawing Sheets

Extract i i i u
Antibody 1 2 ICP10

HERPES SIMPLEX VIRUS TYPE SPECIFIC SEROASSAY

This application claims priority to U.S. Provisional Patent Application Ser. No. 60/036,622, filed Jan. 31, 1997, now abandoned.

BACKGROUND OF THE INVENTION

Humans are infected by two herpes simplex viruses respectively designated HSV-1 and HSV-2. The two viruses have well defined biologic and antigenic differences but are 50% similar at the DNA and protein levels (have 50% type common antigenic determinants). There are 78 proteins which are encoded by the viral DNAs. In most of these, approximately 50% of the antigenic determinants are type-common and they are generally the most antigenic. Only a few proteins have primarily type-specific epitopes.

Mucosal and skin surfaces (generally abraded skin) are the usual site of infection with both of these viruses. The mouth and lips are the most common sites of infection with HSV-1, while HSV-2 is associated with genital infections. Although HSV-1 and HSV-2 are usually transmitted by different routes and involve different areas of the body, there is much overlap between the epidemiology and clinical manifestations of infections caused by these viruses.

Primary infection with HSV-1 generally occurs in children less than 5 years of age where it is often asymptomatic or very mild manifesting as oropharyngeal disease (gingivostomatitis). Primary infection can also occur in young adults where it has been associated with pharyngitis and, often, a mononucleosis-like syndrome. Primary HSV-1 infection leads to virus shedding in the mouth for as long as 23 days, on the average for 7–10 days. Neutralizing antibodies begin to appear on days 4–7 after clinical onset of disease and peak at approximately 3 weeks. Neutralizing antibodies and antibody-dependent cellular cytotoxicity antibodies persist for the lifetime of the host. Virus shedding in the saliva of asymptomatic children was documented in approximately 3–20% of children under 15 years of age. Virus is transmitted from infected to susceptible individuals by respiratory droplets or through direct contact with infected secretions during close personal contact. Primary infection is followed by the establishment of latency with periodic recurrent symptoms. Primary infection with HSV-2 occurs later in life (transmission is generally by sexual contact) and it occurs in the presence of neutralizing antibody to HSV-1. The presence of HSV-1 antibodies prior to infection with HSV-2 generally affects the development of the HSV-2 antibodies.

Studies designed to examine the protein specificity of the antibody response have shown that early after infection antibodies appear to gD, gB, ICP4, gE, gG and gC although not all proteins were studied. The more severe the primary infection or the more frequent the recurrences, the greater the band intensity or the quantity of antibodies. However, the absence of an antibody response (or the enhanced antibody response) to a specific viral protein does not correlate with the severity of the disease or the frequency of recurrences. In fact, the appearance of antibody to a specific protein depends on the inherent antigenicity of the specific protein (as determined after exposure only to that protein) and its presentation to the immune system by professional antigen presenting cells. The levels of expression of the specific protein in virus infected cells is effected by the presence of additional viral proteins. The appearance of antibody to a specific viral protein is further regulated by the previous immune status of the host. For example, antibodies to HSV-2 proteins must develop in a host that already has antibody to the homologous HSV-1 proteins resulting, for at least some of the HSV-2 proteins, in downregulation.

Serologic Assays

A variety of serologic assays are available, although none is currently practical for quantitating type-specific antibodies. Indeed, many assays can give rise to confound the results. Because of the extensive cross-reactivity between the two HSV serotypes, it is difficult to detect HSV-2 antibodies in patients who already have high titers of antibodies to HSV-1 and vice versa. Therefore serodiagnosis is not routinely done in diagnostic laboratories. Available assays include neutralization, complement fixation, passive hemagglutination, antibody-dependent cytotoxicity, ELISA and immunoblots.

Microneutralization, originally used to distinguish between antibody to HSV-1 and HSV-2, has since been shown to suffer from problems due to the presence of type-common antibodies. Another variation on the microneutralization, termed the multiplicity analysis kinetics of neutralization assay (MAKNA) was more specific because it used an artificial mixture consisting of wild type HSV-2 and a HSV-1 mutant which lacks a viral glycoprotein designated gC that primarily induces type specific antibody (Infection and Immunity 40:184 (1983)). The virus mixture used in the MAKNA assay consists of type-common and type-specific antigens. However, the assay is not widely accepted for clinical use because it is very complex and can only be performed in research laboratories.

Recently, immunoblot assays using gG-1/gG-2 have been described as the method of choice for the detection of type specific assays. However, there is a significant body of data which indicate that gG assays have low sensitivity. Thus, in direct comparison experiments, the effectiveness of glycoproteins to induce high titers of serum antibody was ranked as: gD>gB>gI>(gC=gE)>gG>gH (Invest. Ophthalmol. Visual Sci., 36:1352 (1995); J. Virol., 68:2118 (1994)). In a large scale study, among women with gG-2 antibody (measured by immunodot) only 13% reported a history of genital herpes; among men with gG-2 antibody only 19% reported a history of genital herpes, while most of those patients had HSV-2 antibodies. A similar pattern of low sensitivity and moderate specificity was also seen for facial herpes infection and gG-1 antibody and probably reflects the relatively poor antigenicity of gG (J. Am. Med. Assoc., 268:1702 (1992)). Anti-gG-2 antibody was detected only in 47% of cases with HSV-2 infection after a prior HSV-1 infection suggesting that a prior HSV-1 infection modifies the HSV type-specific serological response (J. Gen. Virol., 70:2365 (1989)). Major problems with identification of patients with HSV-1 antibody or dual antibody status using gG was also shown by others (J. Virol. Methods, 18:159 (1987)).

It is, therefore evident that a serologic assay capable of differentiating between HSV-1 and HSV-2 antibody while retaining good sensitivity is not yet available. The methods currently in use in the art lack sensitivity and accuracy. The instant invention solves this problem and provides a highly specific assay using a patient's blood to distinguish HSV-1 antibodies from HSV-2 antibodies.

SUMMARY OF THE INVENTION

It is an object of the present invention to provide a method for distinguishing infection in a subject with HSV-1 or HSV-2 using only a blood test.

It is a further aspect of the invention to provide an assay system which is able to distinguish HSV-1 antibodies from HSV-2 antibodies.

DETAILED DESCRIPTION OF THE INVENTION

Figure 1:
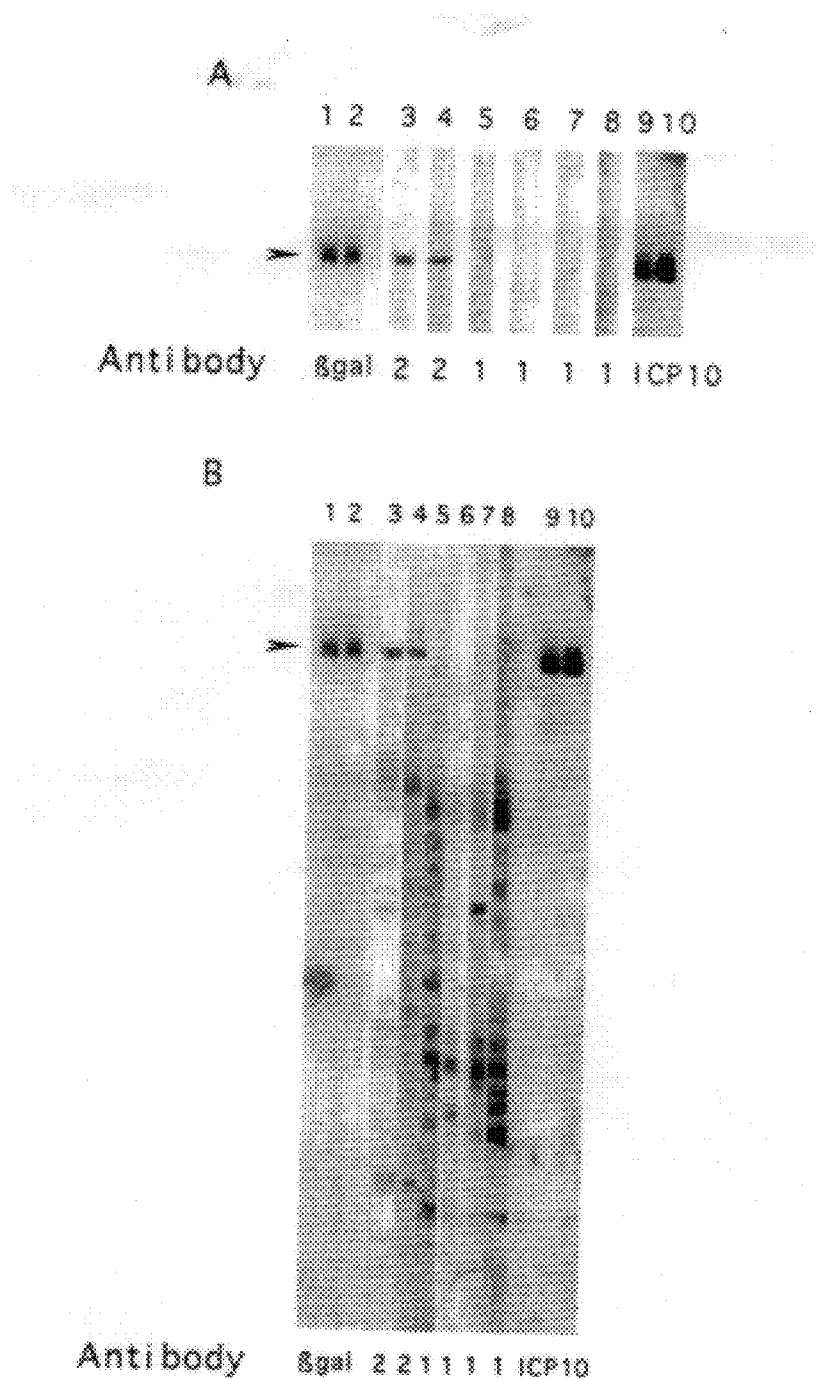
FIG. 1: Western blot assay of HSV patients sera with ARR infected cell extracts. Extracts from ICP10ΔRR infected cells were electrophoresed on 7% polyacrylamide gels and transferred to nitrocellulose membranes. Immunoblotting was done with (lane 1) 1:100 dilution of monoclonal antibody to β-galactosidase, (lane 2) 1:200 dilution of monoclonal antibody to β-galactosidase, (lanes 3–4) 1:100 dilution of sera from patients positive for HSV-2 by virus isolation, (lanes 5–8) 1:100 dilution of sera from patients positive for HSV-1 by virus isolation, (lane 9) 1:200 dilution of anti LA-1 antibody, (lane 10) 1:100 dilution of anti LA-1 antibody, which is specific for ICP10PK amino acids 13–26 (Aurelian et al., "Molecular Diagnostics of Human Cancer. Cancer Cells," Vol. 7, pp.187–191. Cold Spring Harbor Laboratory, Cold Spring Harbor, N.Y. 1989). (A) is section of the blot containing only the ICP1-/β-galactosidase fusion protein (173kD) in (B). (1)=HSV-1 patient's sera and (2)= HSV-2 patient's sera. Arrow denotes the ICP10/β-galactosidase fusion protein.

The present invention provides a unique assay system which distinguishes HSV-1 infection from HSV-2 infection in a highly specific, accurate manner. The inventors have discovered an effective, convenient, and inexpensive serologic assay to distinguish HSV-1 infection from HSV-2 infection. ICP10 is a fusion protein that consists of an amino-terminus domain (PK domain) which is largely HSV type-specific and a carboxy domain (RR domain) that is largely type common. Unlike gG, ICP10 is highly immunogenic. Monoclonal antibodies made in animals given a mixture of total viral proteins (approximately 78) are primarily (approximately 80%) to ICP10 and animals given ICP10 mount high titers of specific antibodies. Given its relatively high antigenicity and type-specificity, the ICP10PK domain (SEQ ID NO.1) is a highly desirable antigen for serologic assays that can differentiate between HSV-2 and HSV-1 antibody. An additional complication with gG is that it is glycosylated and this modification is likely to be essential for optimal antigenicity. Therefore, it cannot be produced in bacteria, where it will not be glycosylated. In infected cells where it will be glycoslation, its purification from virus infected eukaryotic cells is relatively complex.

The HSV-2 recombinant virus designated ICP10ΔRR in which the RR domain of ICP10 has been replaced with the gene that codes for LacZ is used. The construction of this virus is described in Peng et al., Virology 216:184 (1996). This fusion protein is 173kDa. Because in cells infected with the virus for 24–48hrs, there are relatively few proteins of a similar molecular weight and the protein is blue when stained with X-gal, it can be readily isolated from infected cells by various well-known purification methods, such as gel electrophoresis. Antigen can be expressed by a bacterial, viral, fungal, yeast, plant, or animal vectors. It can comprise the entire ICP10PK domain or fractions thereof, alone or fused to various other proteins, beta-galactisidase being the preferred embodiment. Native or denatured antigen can be used. The antigen could be bound to polystyrene or other organic or inorganic particulate forms, either bead shaped or irregular, which can be aggregated with evaluation of the degree of aggregation quantitated visually or spectroscopically The gel isolated fusion protein is used to determine the presence of HSV-2 antibody. The fusion protein is used as an antigen in various serologic assays, including Western blot and blot assays with patient serum and tagged (for example colloidal gold or peroxidase) protein A. Other conjugates can be used to recognize the antigen-antibody complex, including anti-IgG and its subtypes, anti-IgM, anti-IgA, protein G, each of which may be conjugated to a wide array of markers or reporter enzymes for detection, including by way of example and not by way of limitation, glucose oxidase, alkaline phosphatase, luciferase, green fluorescent protein, colloidal gold or carbon. In a spot blot assay, a negative response means no infection with HSV or infection with HSV-1 only.

A competition assay could also be run similarly or with variances in levels to Example 3 where rabbit anti-ICP10 antibody is used at one level which shows that HSV-1 antibody in the human serum did not compete with the detection of the HSV-2 specific antibody.

To determine the presence of antibodies to HSV-1 or both HSV-1 and HSV-2, the gel containing the separated virus proteins is transferred to nitrocellulose and assayed by Western blot. The ICP10 fusion protein is identified by X-gal staining (one blue band). The blot is exposed to the patient serum and the tagged detection system. If the patient has antibody to HSV-1, many bands will become visible but the 173kDa fusion protein will not be recognized. If the fusion protein is recognized together with the other proteins, the patient has antibodies to HSV-2, or both HSV-2 and HSV-1.

Although Western Blot assays are the preferred embodiment, other assays are also envisioned such as immunoprecipitation, a spot blot, a combination of immunoprecipitation and blotting, a direct or indirect ELISA or RIA.

The assay as shown also identifies other proteins that are present in HSV-1 or HSV-2, thus allowing the differentiation of a positive response to either HSV-1 or HSV-2 or both. Detection of the 173 kDa band represents HSV-2 seropositivity whereas detection of other bands in the absence of the 173kDa band indicates a seropositivity for HSV-1.

Example 1 shows a positive correlation of the presence of serum antibody to the ICP10 PK domain which correlates with HSV-2 isolation. It also shows a negative correlation for the presence of serum antibody to this ICP10 domain in patients from whom HSV-1 and not HSV-2 was isolated. The patients from whom HSV-2 was isolated had previously been infected with HSV-1 and had antibody to HSV-1, further confirming the ability of the assay to differentiate antibody to HSV-1 and HSV-2.

The assay can be used as an adjunct of pathology to identify the high risk patient with cervical abnormality. The ICP10 PK domain is the virus oncogene which cross-reacts with the cervical cancer associated oncogene. It has previously been shown that patients with a persistent cervical abnormality (after therapy) have IgM antibody that recognizes the ICP10 PK domain (Aurelian et al., "Molecular Diagnostics of Human Cancer. Cancer Cells," Vol. 7, pp.187–191. Cold Spring Harbor Laboratory, Cold Spring Harbor, N.Y. 1989). The protein can be used in spot blot as described in section I (above) with patient serum and anti-human IgG or anti-human IgM to determine whether the patient has IgG or IgM antibody. An IgM positive response in a woman with abnormal cervical pathology will be indicative of a persistent cervical lesion.

The type-specific serologic assay will be of particular importance in the pregnant woman. Genital HSV infection in the pregnant woman must be considered separately because of the risk to fetus and newborn. A particularly perplexing but uncommon problem encountered with HSV infection during pregnancy is that of widely disseminated disease with mortality among these pregnant women greater than 50%. Fetal deaths have also occurred in more than 50% of cases although mortality did not necessarily correlate with death of the mother. Factors associated with pregnancy may place both mother and fetus at increased risk for severe infection.

Nondisseminated (localized) genital infection is most common form of infection during pregnancy at a frequency of about 1% at any time during gestation. Infection during gestation has been associated with fetal disease in utero. Maternal primary infection before 20 weeks gestation has been associated with spontaneous abortion in 25% of cases. Morbidity of the fetus born to a woman with a primary infection has been documented with manifestations of severe intrauterine growth retardation. Transmission of infection to the fetus is most frequently (80%) related to virus shedding at the time of delivery. The estimated rate of neonatal HSV is 1 in 2000 to 1 in 5000/year. A progressive increase has been noted in some areas with approximate rates of 1 in 1500 deliveries. Overall, with approximately 3.5 million deliveries per year, the US has an estimated 1000–1500 cases of neonatal infection. Clearly, determination of virus excretion at the time of delivery is of utmost importance. However, it has been argued that this is not justified by the relatively low rate of significant disease and the expense associated with virus isolation.

The incidence of virus excretion at delivery for all women, irrespective of past history has been estimated at 0.01–0.39%. In nonpregnant women virus shedding from the cervix occurs in 0.56% of symptomatic infections versus 0.66% of asymptomatic infections. In pregnant women with asymptomatic infections the rate of shedding from the cervix was 0.2–7.4%. Overall this indicates that the rate of shedding from the cervix is low, particularly when related to recurrent infection. Importantly, however, most infants who develop neonatal disease are born to women who are completely asymptomatic for genital herpes infections at the time of delivery and have neither a past history of genital herpes or a sexual partner reporting genital herpes. These women account for 60–80% of all women whose infected children develop infection. In a recent study only 27% of women who delivered children with neonatal disease had a prior history of or evidence of recurrent lesions due to HSV during the current pregnancy. Also, only one half of these latter women reported partners with HSV infection. At present many women with genital HSV elect to be delivered by caesarean rather than undergo the potential risk of exposure of the fetus to the virus at the time of vaginal delivery and the associated potentially devastating results. Accordingly there is an unnecessarily high frequency of caesarean-related problems. The availability of a simple, rapid, non-invasive and relatively cheap assay that could be used to screen for HSV infection, in pregnancy is highly desirable in order to identify the high-risk patient for whom virus detection at the time of delivery is warranted.

The following examples are provided for illustrative purposes only, and are in no way intended to limit the scope of the present invention.

EXAMPLE 1

Vero cells (African Green Monkey Kidney) were grown in a 150 cm$^2$ culture flask in Earles minimal essential medium (EMEM) containing 10% fetal bovine serum (FBS) for one day (90% confluency). Cells were infected with a mixture containing 1 ml of ICP10ΔRR virus (titer 1×10$^8$/ml) and 4 ml Phosphate buffered saline containing 1% bovine albumin (PBS-albumin) and virus was allowed to adsorb for 1 hr at 37° C.

Virus was removed and cells were overlayed with 30 ml of EMEM-10% FBS and incubated for 44 hrs at which time cytopathic effect was complete. Cells were scraped from the flask, and washed 3 times with cold PBS. The pellet was resuspended in 1 ml of RIPA extraction buffer which contains 20 mM Tris-HCl pH 8, 0.15M NaCl, 1% Nonidet P-40, 1% dexycholate, 0.1% sodium dodecyl sulphate, 1mM phenylmethlysulfonyl fluoride, and 10 μg/ml leupeptin. The mixture was incubated on ice for 30 min and then centrifuged in a Sorval RC-2B centrifuge using the SS-34 rotor at 27,000×g for 30 min at 4° C. The supernatant was mixed with an equal volume of denaturing solution which consisted of 150mM Tris-HCL pH 7.0, 5.7% SDS, 14% 2-β mercaptoethanol, 17% sucrose, 0.04% bromthymol blue, and boiled for 5 min at 90° C.

The extract (3.8 mg)was electrophoresed on a 7% polyacrylamide gel and proteins were electrotransferred onto nitrocellulose membranes (Schleicher and Schuell, BA-85, 0.45 micron) overnight at 50 volts. Membranes were incubated in 10 mM Tris-HCl pH7.4, 0.15M NaCl, 0.01% Tween 20 (TNT) containing 5% non fat dried milk (TNT-milk) for 1 hr at room temperature on a shaking platform. Blots were quickly rinsed twice in TNT, and washed once for 15 min and twice for 5 min at room temperature in TNT. The blot was then put into a 45 well miniblotter (Immunetics, Cambridge Mass.) for assays with sera.

Sera were obtained from 4 patients that had been diagnosed with HSV-1 and 2 patients that had been diagnosed with HSV-2 infections by virus isolation. Sera were diluted 1:100 in TNT-milk) and anti LA-1 antibody (polyclonal rabbit antisera specific to amino acid residues 13–26 of ICP10, see Aurelian et al., "Molecular Diagnostics of Human Cancer. Cancer Cells," Vol. 7, pp.187–191. Cold Spring Harbor Laboratory, Cold Spring Harbor, N.Y.1989), monoclonal antibody specific for β-galactosidase were diluted at a 1:100 or 1:200 dilution in TNT-milk. Sera were loaded into the miniblotter and incubated for 1 hr at room temperature. Blots were washed as described above, and incubated with a 1:5000 dilution of protein A peroxidase conjugate (Sigma Chemicals, St. Louis Mo.) for 1 hr at room temperature. Blots were washed once for 15 min, and four times for 5 min with TNT, exposed to Renaissance chemiluminescent reagent for 1 min (Dupont NEN, Boston Mass.) and exposed to X-ray film. See FIG. 1.

EXAMPLE 2

Figure 2:
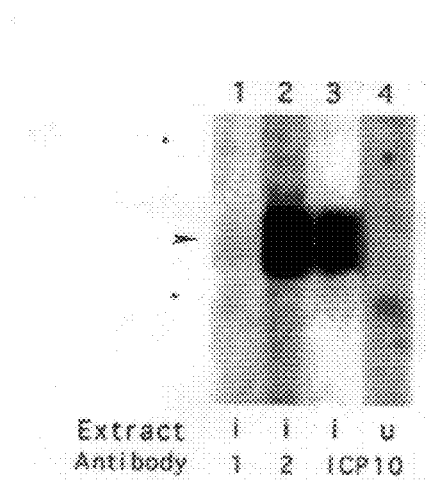
FIG. 2: Western blot assay of HSV patients sera with pp29$^{LA-1}$ bacterial cell extracts. Extracts from *E coli* containing the plasmid pJL11 that were uninduced (u) or induced by growth at 42° C. for 3 hr (i) were electrophoresed on 8.5% polyacrylamide gels and transferred to nitrocellulose membranes. Immunoblotting was done with (lane 1) 1:100 dilution of serum from a patient positive for HSV-1 by virus isolation, (lane 2) 1:100 dilution of serum from a patient positive for HSV-2 by virus isolation, (lanes 3,4) 1:100 dilution of anti LA-1 antibody. (1)=HSV-1 patient's sera (2)=HSV-2 patient's sera. Arrow denotes pp29$^{LA-1}$ protein.

One of the HSV-1 positive and one of the HSV-2 positive by virus isolation patients were also assayed using pp29 bacterial extracts. Plasmid expression vector pJL11 (Luo et al, J. Biol. Chem. 266:20976–20983, 1991) containing *E coli* K-12 DH1 bacteria, were grown in LB medium (1% tryptone, 0.5% yeast extract, 1 mM sodium hydroxide, 170 mM sodium chloride) with 100 μg/ml ampicillin overnight at 37° C., diluted 1:50 in fresh LB medium at 30° C. for 2–3 hr until the optical density reached 0.5. At this time, cultures were incubated at 42° C. for 3 hr to induce expression, bacteria were collected by centrifugation (5,000×g, 10 min), and resuspended in 1/100 volume of 50 mM Tris-HCl pH 7.4, 10 mM EDTA, 1 mM PMSF, 10 mM benzamidine, 30 μg/ml leupeptin and 2 mg/ml lyzozyme and incubated on ice for 15 min. n-Octyl β-D-glucopyranoside (Sigma Chemicals) (1/8 volume) and NaCl (1M final concentration) were added and the mixture was incubated on ice for an additional 15 min. The mixture was sonicated for 2 min at 40° C., and cell debris was removed by centrifugation at 22,000×g in a SS-34 rotor for 1 hr. The supernatant was diluted 1:55 in gel denaturing buffer and 8.5 mg of extract was loaded onto a 8.5% acrylamide gel and electrophoresed, and electrotransferred to nitrocellulose membranes as described in Example 1. Immunoblotting was as described in Example 1 with patients'sera diluted 1:100 and anti LA-1 antibody diluted 1:100 in TNT-milk. See FIG. 2.

EXAMPLE 3

Figure 3:
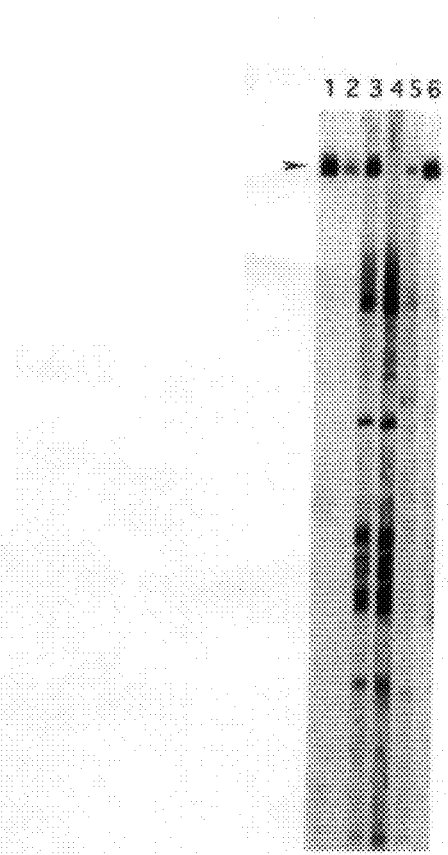
FIG. 3: Competition western blot assay with a serum from an HSV-1 patient and anti LA-1 antibody. Extracts from ICP10ΔRR infected cells were electrophoresed on 7% polyacrylamide gels and transferred to nitrocellulose membranes. Immunoblotting was done with (lane 1) 1:100 dilution of anti LA-1 antibody, (lane 2) 1:100 dilution of monoclonal antibody to β-galactosidase, (lane 3) 1:100 dilution of serum from a patient positive for HSV-1 ny virus isolation mixed with a 1:200 dilution of anti LA-1 antibody, (lane 4) 1:100 dilution of the same serum in lane 3 with no anti LA-1 antibody (lane 5) 1:100 dilution of serum from a patient positive for HSV-2 by virus isolation, (lane 6) 1:100 dilution of anti LA-1 antibody. Arrow denotes the ICP10/β-galactosidase fusion protein.

An extract from ICP10ΔRR infected cells was prepared, electrophoresed, and transferred to nitrocellulose membranes as described in Example 1. Immunoblotting was as described in Example 1 with serum from an HSV-1 positive patient by virus isolationdiluted 1:100 and the same diluted sera mixed with a 1:200 dilution of anti LA-1 antibody. A 1:100 dilution of serum from an HSV-2 positive patient, anti LA-1 antibody, and monoclonal antibody specific for β-galactosidase were also assayed. See FIG. 3.

All references cited herein are incorporated by reference in their entirety.

While the invention has been described in detail, and with reference to specific embodiments thereof, it will be apparent to one with ordinary skill in the art that various changes and modifications can be made therein without departing from the spirit and scope thereof.

What is claimed:

1. A method for distinguishing between HSV-1 and HSV-2 antibodies in a serum sample comprising the steps of:

(a) contacting the serum with an antigen comprising the protein kinase domain of the ICP10 subunit of HSV-2 (SEQ. ID. NO.1) having a marker fused thereto;

(b) using said antigen to detect the presence of HSV-2 antibody in the serum the HSV-2 antibody recognizing said antigen and binding thereto; and c) examining the antigen for the presence of said bound antibody, wherein the presence of said bound antibody indicates the presence of HSV-2 antibody in serum.

2. The method of claim 1 wherein said examining is by a method selected from the group consisting of Western blots, immunoprecipitations, spot blots, direct ELISAs, indirect ELISAs, direct RIAs, indirect RIAs, competition assays, and combinations thereof.

3. The method of claim 1, wherein said protein is immobilized on a substrate.

4. The method of any of claim 3, wherein the substrate is polystyrene.

5. The method of any of claim 3, wherein the substrate is an organic particulate.

6. The method of any of claim 3, wherein the substrate is an inorganic particulate.

7. The method of claim 5, wherein said particulate is bead shaped.

8. The method of claim 6, wherein said particulate is irregular.

9. The method of claim 1 wherein the examining is visual.

10. The method of claim 1, wherein the examining is spectroscopic.

11. The method of claim 1 wherein said marker is selected from the group consisting of beta-galactosidases, colloidal golds, peroxidases, carbons, gluocose oxidases, alkaline phosphatases, luciferases and, green fluorescent proteins.

12. The method of claim 1 wherein said marker is beta-galactosidase.

13. A kit for detecting the presence of HSV-2 antibodies consisting essentially of:
 (a) an antigen comprising the protein kinase domain of the ICP10subunit of HSV-2 (SEQ. ID. NO. 1) having a marker fused thereto;
 (b) serologic assay components; and
 (c) written instructions for using said antigen for detecting the presence of HSV-2 antibody in a serum sample the HSV-2 antibody recognizing said antigen and binding thereto, and examining the antigen for the presence of said bound antibody, wherein the presence of said bound antibody indicates the presence of HSV-2 antibody in serum,
 wherein anti-human IgG or anti-human IgM antibodies are specifically absent from said kit.

14. The kit of claim 13, wherein said assay is selected from the group consisting of Western blots, immunoprecipitations, spot blots, direct ELISAs, indirect ELISAs, direct RIAs, indirect RIAs, competition assays, and combinations thereof.

15. The kit of claim 13, wherein said marker is selected from the group consisting of beta-galactosidases, colloidal golds, peroxidases, carbons, gluocose oxidases, alkaline phosphatases, luciferases, and green fluorescent proteins.

* * * * *

SEQUENCE LISTING

```
<160> NUMBER OF SEQ ID NOS: 1

<210> SEQ ID NO 1
<211> LENGTH: 448
<212> TYPE: PRT
<213> ORGANISM: herpes simplex virus-2
<220> FEATURE:
<221> NAME/KEY: DOMAIN
<222> LOCATION: (1)..(446)
<223> OTHER INFORMATION: PROTEIN KINASE DOMAIN OF ICP10 SUBUNIT OF HSV-2
<300> PUBLICATION INFORMATION:
<301> AUTHORS: CHUNG ET AL.,
<303> JOURNAL: J. Virol.
<304> VOLUME: 63
<306> PAGES: 3389-3398
<307> DATE: 1989
<300> PUBLICATION INFORMATION:
<301> AUTHORS: NELSON ET AL.,
<303> JOURNAL: J. Biol. Chem.
<304> VOLUME: 271
<306> PAGES: 17021-17027
<307> DATE: 1996

<400> SEQUENCE: 1

Met Ala Asn Arg Pro Ala Ala Ser Ala Leu Ala Gly Ala Arg Ser Pro
 1               5                  10                  15

Ser Glu Arg Gln Glu Pro Arg Glu Pro Glu Val Ala Pro Pro Gly Gly
             20                  25                  30

Asp His Val Phe Cys Arg Lys Val Ser Gly Val Met Val Leu Ser Ser
         35                  40                  45

Asp Pro Pro Gly Pro Ala Ala Tyr Arg Ile Ser Asp Ser Ser Phe Val
     50                  55                  60

Gln Cys Gly Ser Asn Cys Ser Met Ile Ile Asp Gly Asp Val Ala Arg
```

-continued

```
                65                  70                  75                  80
Gly His Leu Arg Asp Leu Glu Gly Ala Thr Ser Thr Gly Ala Phe Val
                    85                  90                  95
Ala Ile Ser Asn Val Ala Ala Gly Gly Asp Gly Arg Thr Ala Val Val
                100                 105                 110
Ala Leu Gly Gly Thr Ser Gly Pro Ser Ala Thr Thr Ser Val Gly Thr
                115                 120                 125
Gln Thr Ser Gly Glu Phe Leu His Gly Asn Pro Arg Thr Pro Glu Pro
                130                 135                 140
Gln Gly Pro Gln Ala Val Pro Pro Pro Pro Pro Pro Phe Pro Trp
145                 150                 155                 160
Gly His Glu Cys Cys Ala Arg Arg Asp Ala Arg Gly Gly Ala Glu Lys
                    165                 170                 175
Asp Val Gly Ala Ala Glu Ser Trp Ser Asp Gly Pro Ser Ser Asp Ser
                180                 185                 190
Glu Thr Glu Asp Ser Asp Ser Ser Asp Glu Asp Thr Gly Ser Gly Ser
                    195                 200                 205
Glu Thr Leu Ser Arg Ser Ser Ile Trp Ala Ala Gly Ala Thr Asp
                210                 215                 220
Asp Asp Asp Ser Asp Ser Asp Ser Arg Ser Asp Asp Ser Val Gln Pro
225                 230                 235                 240
Asp Val Val Val Arg Arg Arg Trp Ser Asp Gly Pro Ala Pro Val Ala
                    245                 250                 255
Phe Pro Lys Pro Arg Arg Pro Gly Asp Ser Pro Gly Asn Pro Gly Leu
                    260                 265                 270
Gly Ala Gly Thr Gly Pro Gly Ser Ala Thr Asp Pro Arg Ala Ser Ala
                    275                 280                 285
Asp Ser Asp Ser Ala Ala His Ala Ala Pro Gln Ala Asp Val Ala
                290                 295                 300
Pro Val Leu Asp Ser Gln Pro Thr Val Gly Thr Asp Pro Gly Tyr Pro
305                 310                 315                 320
Val Pro Leu Glu Leu Thr Pro Glu Asn Ala Glu Ala Val Ala Arg Phe
                    325                 330                 335
Leu Gly Asp Ala Val Asp Arg Glu Pro Ala Leu Met Leu Glu Tyr Phe
                    340                 345                 350
Cys Arg Cys Ala Arg Glu Glu Ser Lys Arg Val Pro Pro Arg Thr Phe
                355                 360                 365
Gly Ser Ala Pro Arg Leu Thr Glu Asp Asp Phe Gly Leu Leu Asn Tyr
                370                 375                 380
Ala Leu Ala Glu Met Arg Arg Leu Cys Leu Asp Leu Pro Pro Val Pro
385                 390                 395                 400
Pro Asn Ala Tyr Thr Pro Tyr His Leu Arg Glu Tyr Ala Thr Arg Leu
                405                 410                 415
Val Asn Gly Phe Lys Pro Leu Val Arg Arg Ser Ala Arg Leu Tyr Arg
                    420                 425                 430
Ile Leu Gly Ile Leu Val His Leu Arg Ile Arg Thr Arg Glu Ala Ser
                    435                 440                 445
```